(12) United States Patent
Badr et al.

(10) Patent No.: US 7,566,310 B2
(45) Date of Patent: Jul. 28, 2009

(54) SYSTEM FOR DIAGNOSING AND TREATING SLEEP APNEA

(75) Inventors: M. Safwan Badr, West Bloomfield, MI (US); Khaled F. Mansour, Dearborn, MI (US); James A. Rowley, West Bloomfield, MI (US); Mahdi A. Shkoukani, Macomb Township, MI (US)

(73) Assignee: Wayne State University, Detroit, MI (US)

( * ) Notice: Subject to any disclaimer, the term of this patent is extended or adjusted under 35 U.S.C. 154(b) by 440 days.

(21) Appl. No.: 10/523,743

(22) PCT Filed: Aug. 1, 2003

(86) PCT No.: PCT/US03/24188

§ 371 (c)(1),
(2), (4) Date: Nov. 14, 2005

(87) PCT Pub. No.: WO2004/012597

PCT Pub. Date: Feb. 12, 2004

(65) Prior Publication Data

US 2006/0241509 A1 Oct. 26, 2006

Related U.S. Application Data

(60) Provisional application No. 60/400,038, filed on Aug. 2, 2002.

(51) Int. Cl.
*A61B 5/08* (2006.01)

(52) U.S. Cl. .................................. 600/538; 600/529
(58) Field of Classification Search .......... 600/529–543
See application file for complete search history.

(56) References Cited

U.S. PATENT DOCUMENTS

| | | | |
|---|---|---|---|
| 4,802,492 A | 2/1989 | Grunstein | |
| 5,617,846 A | 4/1997 | Graetz | |
| 6,068,602 A * | 5/2000 | Tham et al. | 600/533 |
| 6,142,952 A | 11/2000 | Behbehani | |
| 6,342,040 B1 * | 1/2002 | Starr et al. | 600/538 |

FOREIGN PATENT DOCUMENTS

GB 2 077 444 A 12/1981

* cited by examiner

*Primary Examiner*—Charles A Marmor, II
*Assistant Examiner*—Christian Y Jang
(74) *Attorney, Agent, or Firm*—Rohn & Monsanto, PLC

(57) ABSTRACT

Two programs measure upper airway resistance using Resistance=Pressure/Flow. Raw flow and pressure data is divided into breaths and time adjusted so each breath starts with the value zero. Each breath is graphed as flow in the y-axis and time in the x-axis. The slope between points Flow=0 and Flow=0.20 is calculated. The resistance is the inverse of the slope. The second program determines whether a breath is flow limited or not. It also uses the flow and time data to perform a curve fitting to describe the flow-time in meaningful polynomial function $F(P)=A t^3+B t^2+Ct+D$. The derivative of this function is $F'=3At^2+2Bt+C$. If the value of the derivative F' at maximum flow is less than or equal zero, then it is a flow limited breath, otherwise, it is non flow limited breath. Also, the need for a pressure-monitoring catheter is obviated.

30 Claims, 6 Drawing Sheets

FIG. 5A
FIG. 5B
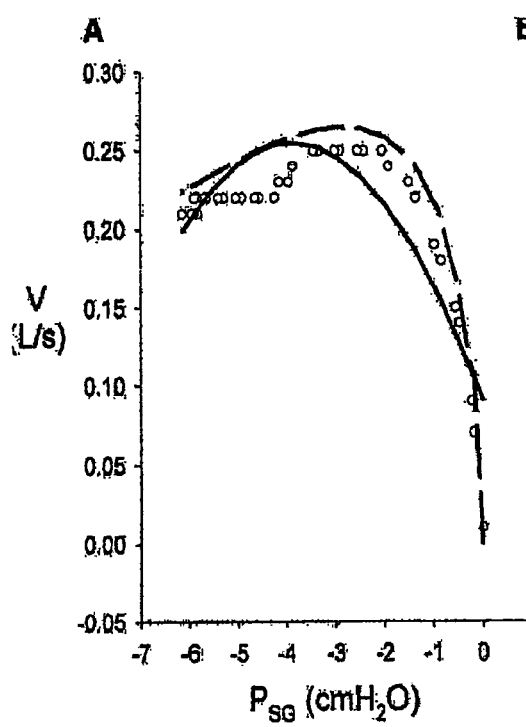
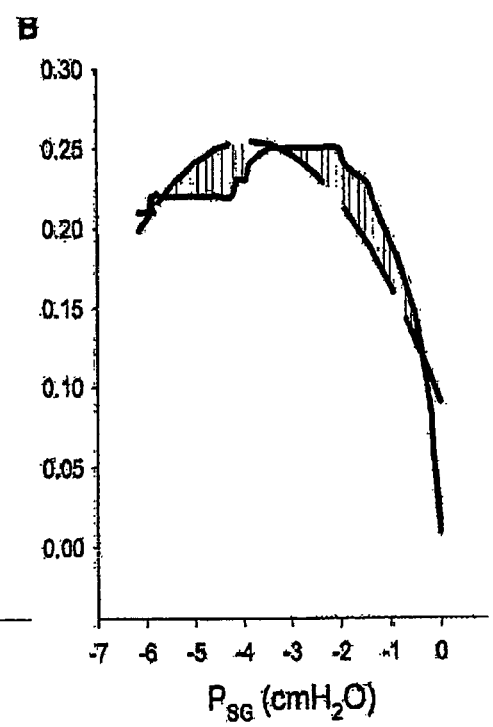

SYSTEM FOR DIAGNOSING AND TREATING SLEEP APNEA

RELATIONSHIP TO OTHER APPLICATION

This application is a U.S. national stage filing under 35 U.S.C. § 371 of International Application No. PCT/US2003/024188 filed on Aug. 1, 2003 and claims the benefit of the filing date of Provisional Application for U.S. Letters Patent Ser. No. 60/400,038 on Aug. 2, 2002 in the name of the inventors herein.

GOVERNMENT RIGHTS

A portion of this invention was made under contract of appointment awarded by The John D. Dingell Veterans Administration Medical Center in Detroit, Mich. wherein one or more inventors herein stand appointed by the Veterans Administration ("VA") to perform work on behalf of the VA in its facilities. As such, the VA appointed inventor(s) are subject to the federal laws applicable to inventions and discoveries made in the course of the VA appointment. The government has certain rights in the corresponding portion of the present invention.

BACKGROUND OF THE INVENTION

1. Field of the Invention

This invention relates generally to systems for diagnosing sleeping disorders, and more particularly, to a system that is useful in effecting rapid diagnosis of, and providing controlled therapy to, patients who suffer from sleep apnea.

2. Description of the Related Art

There is a need in the present state of the art of diagnosing sleeping disorders for automated non-invasive methods that yield objective and reproducible data responsive to the presence of inspiratory flow limitation during sleep. There is a particular need for a system that can perform the necessary acquisition of such data without requiring the use of a pressure-monitoring catheter in the pharynx of the patient.

From the anatomical standpoint, the airways consist of upper and lower airways. Sleep apnea is a common condition that is characterized by obstruction or narrowing of the upper airway. The upper airway segments are the nose, the mouth, and the larynx. The larynx opens to the trachea and branches into two bronchi. Each bronchi enters a lung and terminates in the alveoli. The analysis that is presented herein in support of the present invention focuses on the pharyngeal upper airway. This upper airway consists of the extrthoracic trachea, the larynx, pharynx, and the nose. The principal site for upper airway closure or narrowing during sleep is the pharynx, which is a heterogeneous structure, and it is part of the pharyngeal airway.

The pharyngeal airway is divided into four segments. These segments are the nasopharynx, the velopharynx, the oropharynx, and the hypopharynx. During inspiration, the pharyngeal structure moves forward toward the center of the lumen.

In addition, more than twenty skeletal muscles surround the pharyngeal airway, the muscles being functionally designated as "dilator" muscles and "constrictor" muscles. The pharyngeal muscles receive aphasic activation during inspiration and support a patent pharyngeal lumen through which air flows. Contraction of the pharyngeal muscles can dilate and stiffen the pharyngeal airway, and the constrictor muscles can improve the upper airway patency. The tongue comprises a highly mobile structure that can occlude the pharyngeal airway and the soft palate, which are important in maintaining upper airway patency. It is also known that the tongue is a major muscle comprising protrude and retractor muscles. Either co-activation of the protrude and the retractor muscles, or independent activation of the protrude muscles, can improve upper airway flow mechanics. Co-activation decreases pharyngeal collapsibility but does not dilate the pharyngeal airway. activation of the tongue protrude muscles results in enlargement of the upper airway.

Before describing the art in greater detail, it may be useful to identify some of the acronyms that are widely used:

| Acronym | Definition |
| --- | --- |
| AHI → | Apnea-hypopnea index |
| ANOVA → | Analysis of Variance |
| CHF → | Chronic Heart Failure |
| CPAP → | Continuous Positive Airway Pressure |
| cRUA → | Calculated Upper Airway Resistance |
| DME → | Therapeutic Products from a Reseller |
| DTC → | Direct to Consumer |
| EEG → | Electroencephalography |
| EMG → | Electromyography |
| EOG → | Electrooculography |
| FOT → | Forced Oscillation Impedance |
| IFL → | Inspiratory Flow Limitation |
| IHD → | Ischemic Heart Disease |
| IPS → | DeVilbiss Internet Processing Software |
| MEMS → | Micromachined Electro-mechanical Pressure Sensors |
| mRUA → | Measured Upper Airway Resistance |
| NIFL → | Non-Flow Limited |
| NPV → | Negative Predictive Value |
| NREM → | Stage 2 sleep (non-REM?) |
| OSA → | Obstructive Sleep Apnea |
| PAP → | Positive Airway Pressure |
| PAT → | Peripheral Arterial Tone |
| PPV → | Positive Predictive Value |
| PSG → | Polysomnography |
| REM → | Rapid Eye Movement sleep |
| RUA → | Upper Airway Resistance |
| SDB → | Sleep-Disordered Breathing |
| SPC → | Superior Pharyngeal Constrictor |
| UARS → | Upper Airway Resistance Syndrome |

Studies of OSA subjects indicate that activation of the superior pharyngeal constrictor ("SPC") muscle is similar to the action of pharyngeal dilator muscles during spontaneous and induced apneas. However the effect of each single muscle in regard of sleep obstruction is not yet clear. It has been reported that the mechanical properties of the upper airway is independent of the dilator skeletal muscles that surround it. Also, the prior art is asserted to have determined that pressure is correspondingly equivalent to volume expansion. In other words, although the specific effect of each muscle is not clear in the present state of the art, the ratio of pressure to volume expansion is 1:1, irrespective of whether the dilator muscles are in active or passive conditions.

Inspiratory flow limitation ("IFL") is the mechanical corollary of snoring and corresponds to a narrowing of the upper airway of a patient. The detection of inspiratory flow limitation will improve the diagnosis of sleep disordered breathing. In the present state of the art, the detection of inspiratory flow limitation typically is achieved by a trained observer who analyzes each breath individually. Such a trained observer will study visually the shape of the time-flow curve that characterizes each breath under consideration. This labor intensive methodology, particularly since it applies a measure of subjectivity to a relatively few breaths, is not adequately precise to achieve an objective and fully reproducible determination of the presence of air flow limitation, and will often result in false diagnoses.

There are available in the art standardized procedures for detecting flow limitation based on analysis of the pressure-flow aspect of the respiration cycle. The known methods, however, are practicable only in sleep research laboratories, and typically are not available in the clinical sleep lab. In the clinical environment, a physician typically will spend about two hours to analyze only about 40 patient breaths. Clearly, the known process is time consuming, functions on a very limited data set, and is likely to produce erroneous results.

Obstructive steep apnea is a condition that is characterized by cessation of breathing during sleep, the air flow being obstructed in the upper airway of the subject. IFL during sleep is defined as decreasing supraglottic pressure without corresponding increase in airway flow rate. This condition generally causes repetitive disturbances during sleep resulting from inadequate flow of air into the lungs of the subject. It is known in the art that resistance to the flow of air is increased during the transition from a state of wakefulness to sleep. A characteristic cross-sectional area can readily be determined in relation to the linear portion of the pressure-flow loop, i.e., corrsponding to a progressive increase in air flow resistance.

There is present in this model a coupling condition that is responsive to the characteristics of the solid structure (i.e., tissue and muscles) of the upper airway and the air flow. The solid structure is characterized by the arrangement of the muscles, the tissue structure, and the viscous flow, which is the air flow. The state of the art is such that there is no indication that muscles affect the compliance of upper airway. The foregoing notwithstanding, the entire solid tissue structure might have a significant effect on obstruction depending upon the viscoelastic properties. However, since such viscoelastic properties of the upper airway have not been thoroughly studied in the relevant literature, it is expected that an analysis based on such properties would have unacceptable uncertainties in its results. Accordingly, greater certainty is achieved if the analysis approaches the problem from the standpoint of air flow in a collapsible tube.

Upper airway obstruction can be caused by several factors. For example, studies have shown that patient with obstructive sleep apnea have an upper airway cross sectional area that is less than that of normal subjects. Therefore, subjects with small upper airway cross sectional area are more likely to have sleep obstruction.

Adipose tissue is the connective tissue in which fat is stored. This tissue surrounds the pharyngeal upper airway, and it has been asserted that this fat might, due to gravity and mass loading that act on the lumen, reduce the upper airway cross sectional area. Other studies, however, assert afinding that the deposit of fact is not related to the pharyngeal narrowing. Instead, the narrowing depends on the thickness of the muscles. Yet another study shows that there are more fat deposits around the collapsible pharyngeal upper airway in patients diagnosed with obstructive sleep apnea, compared to normal subjects. The cross sectional area of patients with Obstructive Sleep Apnea (OSA) is also less than normal during wakefulness. The foregoing notwithstanding, the mechanical effect resulting from fats deposits has not yet been determined.

Mucosal adhesive forces have been considered in the art. The wall of the upper airway has a lining of mucus. It has been hypothesized that surface adhesive forces plays an important role in determining the mechanical properties of the upper airway. During narrowing this mucus lining add more thickness to the surface of the wall, and correspondingly, surface adhesive forces increase the pressure. Surface adhesive forces are considered important in determining the magnitude of the opening pressure required to prevent the mucus from maintaining contact. In animal experiments, it was found that adding topical lubricant to the upper airway reduce the severity It has also been suggested that decreasing the adhesive characteristic of the surface forces will render the upper airway more resistive to collapsing. Thus, it has been hypothesized that the secretion of the mucus could be an important factor during closure of the upper airway, because this will determine the magnitude of the air pressure required to reopen the airway. In sum, however, the physics in support of reduction of the adhesive forces has yet to be explained.

Others in the art have asserted that pressure gradient (i.e., transmural pressure), plays a role in in the collapsibility of the upper airway. Transmural pressure is the pressure difference between intraluminal pressure (pressure inside the lumen), and the extraluminal pressure (atmospheric pressure). During inspiration the pressure in the pharyngeal upper airway is reduced as the cross sectional area is decreased, and the velocity of the air is correspondingly increased. As the pressure in the thorax region increases negatively in relation to atmospheric pressure, the velocity of the air is reduced. The pressure-velocity relationship is consistent with the well-known Bernoulli equation. Thus, a reduction in the transmural pressure will result in a decreased cross-sectional area. The transmural pressure is defined as intraluminal pressure ($P_i$) minus surrounding tissue pressure ($P_t$). Cross sectional area can be minimized as the transmural pressure decreases. The prior art has speculated that the reduction or occlusion in the luminal cross-section is a result of negative intraluminal pressure, or positive ($P_t$). Therefore, as transmural pressure ($P_{tm}$) increases, the cross sectional area increases, and vice versa. During narrowing the intraluminal pressure is always negative, and tissue pressure is positive (with respect to atmospheric pressure).

Thoracic caudal traction is caused by inspiratory thoracic activity resulting from an increase in the cross-section of the upper airway. Caudal traction has two mechanisms. The first mechanism is characterized by the stiffening of the upper airway as longitudinal tension is applied to the upper airway. The second mechanism is the dilation of the pharyngeal airway. It has been reported in the art that caudal traction might transmit sub-atmospheric pressure to the tissue that surrounds the upper airway. In this situation the transmutable pressure increases, whereby the difference between intraluminal pressure, and tissue pressure increases radially, ($P_{tm} = P_{interluminal} - P_{tissue}$) and the collapsibility of the upper airway decreases. Others have found an increase in the maximum inspiratory flow upon observing a decrease in the collapsibility of the upper airway with tracheal displacement. Caudal traction has been shown to increase the maximum $V_{I\,Max}$ inspiratory flow at all levels of tongue displacement. $V_{I\,Max}$ was noticeably increased for each tongue and caudal displacement interaction. Caudal displacement affects the critical pressure response of the tongue displacement. Thus, under caudal traction there is observed a corresponding decrease in the critical value, while the tongue was displaced.

Upper airway resistance is an important mechanical characteristic for the airflow in the upper airway. Resistance has been described as an indirect measure for upper airway caliber, and has been asserted to be the most significant factor in determining the upper airway caliber, as measured on the linear portion of the pressure-flow curve. However, the determination of resistance is not valid if flow limitation is present because pressure and flow are not associated any more.

It has been reported that the resistance of the upper airway increase more than normal prior to obstruction. Upper airway resistance syndrome is characterized by repetitive episodes of IFL, and decreases in esophageal pressure leading to recurrent arousal. High upper airway resistance can cause tiredness, excessive daytime sleepiness, and a change in blood pressure. Subjects with high resistance work harder at breathing. It also has been reported that a significant increase in expiratory resistance occurs in such subjects just before the initial occluded inspiratory effort of occlusive apnea obstructive sleep apneas.

Resistance is defined as $\Delta P/\Delta F$, where $\Delta P$ is the pressure gradient, and $\Delta F$ is the flow. There is generally an increase of resistance during transition from wakefulness to sleep. The linear resistance at flow=0.2 l/s as an accepted reference standard. However there is not available in the art adequate literature that can relate resistance to the linear portion of the pressure flow relationship. Some researchers in the art have reported that upper airway resistance could be infinite in patients that have severe narrowing or closure. This condition appears mostly with patients having obstructive sleep apnea/hypopnea.

None of the researchers relate the flow to pressure in laminar or turbulent flow to determine the linear resistance. According to known principles of fluid mechanics, linear resistance usually occurs in the laminar region. Usually linear resistance indicates a progressive decrease in the cross-sectional area at the linear portion of pressure flow loop. Resistance and cross-sectional area are related by the known Poiselle equation in the linear region. Therefore it is important to find an objective method to determine resistance.

The literature that comprises the known prior art indicates that there is not available an objective methodology for determining resistance or inspiratory flow limitation.

It is, therefore, an object of this invention to provide a reduction in the time required to diagnose whether a patient suffers from IFL.

It is another object of this invention to provide a methodology that produces an objective diagnosis of sleep apnea.

It is also an object of this invention to provide a method of diagnosing sleep apnea without requiring the use of a pressure-monitoring catheter.

It is a further object of this invention to provide a methodology that produces an objective determination of airway resistance in a patient.

It is additionally an object of this invention to provide a diagnostic methodology that distinguishes between laminar and turbulent flow in the upper airway of a patient.

It is yet a further object of this invention to provide objective characterization of a sleep apnea condition that will be useful in controlling a therapy therefor.

SUMMARY OF THE INVENTION

The foregoing and other objects are achieved by this invention which provides a method of measuring upper airway resistance of a human patient. In accordance with a first method aspect of the invention, there are provided the steps of:

obtaining air pressure data from an air pressure data signal corresponding to a plurality of breathing cycles while the human patient is asleep;

obtaining air flow data from an air flow data signal corresponding to the plurality of breathing cycles while the human patient is asleep;

transferring the air pressure data and the air flow data to a processor;

storing the air pressure data and the air flow data in respective correlated storage regions of a matrix program system of the processor;

segregating the air pressure data and the air flow data in the matrix program of the processor into corresponding breathing cycles of the human patient;

computing normalized air pressure data to achieve a predetermined normalized air pressure value to correspond with a predetermined point for each breathing cycle of the human patient;

producing a correlation of the air flow data against normalized air pressure data;

curve-fitting onto the correlation of the air flow data against normalized air pressure data a curve corresponding to a predetermined multiple term mathematical function;

computing the value of the coefficients of the predetermined multiple term mathematical function; and computing the derivative of the predetermined multiple term mathematical function.

In a specific illustrative embodiment of the invention of this first method aspect there is provided in the step of curve-fitting onto the correlation of the air flow data against normalized air pressure data a curve, the predetermined multiple term mathematical function is a quadratic function, $F(P)=AP^2+BP+C$, where A, B, and C are coefficients.

In a further embodiment, the step of curve-fitting onto the correlation of the air flow data against normalized air pressure data a curve, the predetermined multiple term mathematical function is a three term polynomial function $F(P)=AP^3+BP^2+CP+D$, where A, B, C, and D are coefficients. The derivative of the three term polynomial function corresponds to the relationship:

$$\frac{dF}{dP} = 3AP^2 = 2BP + C.$$

There is additionally provided the step of determining that a breath is inspiratory in response to the derivative of the three term polynomial function having a value of zero or positive, whereby $$\frac{dF}{dP} \geq 0 \rightarrow IFL.$$

A breath is inspiratory in response to the derivative of the three term polynomial function having a negative value, whereby $$\frac{dF}{dP} < 0 \rightarrow NIFL.$$

The resistance is computed in response to the reciprocal of coefficient C, whereby Resistance=1/C.

In accordance with a second method aspect of the invention, there is provided a method of determining a flow-limiting characteristic of the upper airway of a human patient, the method including the steps of:

obtaining air pressure data from an air pressure data signal corresponding to a plurality of breathing cycles while the human patient is asleep;

obtaining air flow data from an air flow data signal corresponding to the plurality of breathing cycles while the human patient is asleep;

transferring the air pressure data and the air flow data to a processor;

storing the air pressure data and the air flow data in respective correlated storage regions of a matrix program system of the processor;

segregating the air pressure data and the air flow data in the matrix program of the processor into corresponding breathing cycles of the human patient;

computing normalized air pressure data to achieve a predetermined normalized air pressure value to correspond with a predetermined point for each breathing cycle of the human patient; and computing the flow-limiting characteristic of the upper airway of a human patient as a function of normalized air pressure data divided by corresponding air flow data.

In a specific illustrative embodiment of the invention of this second method aspect, the matrix program system is a spreadsheet program system, and the air pressure data and the air flow data being arranged in respective spreadsheet columns correlated by rows. Normalized air pressure data is stored in a respective spreadsheet column correlated by rows into corresponding breathing cycles of the human patient.

Each breathing cycle of the human patient is determined in relation to the predetermined point thereof corresponding to the predetermined normalized air pressure value. Generally, inspiration precedes expiration, and flow is zero at the commencement of the breath cycle. In addition, the predetermined normalized air pressure value corresponds to a zero value. There is further provided the step of computing the flow-limiting characteristic of the upper airway of a human patient for each of the plurality of breathing cycles. The air pressure data and the air flow data are sampled a plurality of times during each breathing cycle. Also, the step of computing the flow-limiting characteristic of the upper airway of a human patient is performed a corresponding plurality of times during each breathing cycle. The step of computing the flow-limiting characteristic of the upper airway of a human patient is performed a corresponding plurality of times during each breathing cycle and during which the air flow data has a predetermined value. The air flow data and the normalized pressure data are correlated to form a data correlation in a data correlation array, and the predetermined value of the air flow data is determined within a substantially linear portion of the data correlation. The predetermined value of the air flow data is approximately between 0.00 L/s and 0.22 L/s, and the predetermined value of the air flow data is approximately 0.20 L/s.

In a further embodiment, there is provided the further step of computing a slope of the correlated air flow data and normalized pressure data within the substantially linear portion of the data correlation. A data array is produced corresponding to the flow-limiting characteristic wherein the normalized air pressure data corresponds to the x-axis and the air flow data corresponds to the y-axis.

In accordance with a third method aspect of the invention, there is provided a method of measuring upper airway resistance of a human patient, the method is provided with the steps of:

obtaining air pressure data from an air pressure data signal corresponding to a plurality of breathing cycles while the human patient is asleep;

obtaining air flow data from an air flow data signal corresponding to the plurality of breathing cycles while the human patient is asleep;

transferring the air pressure data and the air flow data to a processor;

storing the air pressure data and the air flow data in respective correlated storage regions of a matrix program system of the processor;

segregating the air pressure data and the air flow data in the matrix program of the processor into corresponding breathing cycles of the human patient;

computing normalized air pressure data to achieve a predetermined normalized air pressure value to correspond with a predetermined point for each breathing cycle of the human patient;

producing a correlation of the air flow data against normalized air pressure data;

curve-fitting onto the correlation of the air flow data against normalized air pressure data a curve corresponding to a three term polynomial function $F(P)=AP^3+BP^2+CP+D$, where A, B, C, and D are coefficients; and computing the value of the upper airway resistance of a human patient as an inverse function of coefficient C of the three term mathematical function, C, whereby Resistance=1/C.

Each breathing cycle is defined at an onset point where inspiratory flow is zero. Moreover, each breathing cycle is defined at an onset point where supraglottic pressure has been normalized to zero. The derivative of the three term polynomial function is computed in accordance with the relationship:

$$\frac{dF}{dP} = 3AP^2 + 2BP + C.$$

Then, the presence of inspiratory flow limitation is determined in response to the derivative of the three term polynomial function.

In a specific illustrative embodiment of the invention, the step of obtaining air flow data from an air flow data signal includes the further step of recording the air flow data signal on a polygraph. Additionally, the step of storing the air pressure data and the air flow data in respective correlated storage regions of a matrix program system of the processor include the step of exporting the air pressure data and the air flow data to a first Excel® spreadsheet. Then, a graphical representation of adjusted time along the x-axis and flow along the y-axis is plotted. There is then performed a step of curve fitting an inspiratory rising limb flow-time curve to a mathematical polynomial function $F(P)=A\ t^3+B\ t^2+Ct+D$, where A, B, C, and D are coefficients. The derivative of the mathematical polynomial function is then calculated, and the value of the derivative of the mathematical polynomial function is exported to a second Excel® spreadsheet. Whether a breath is or is not flow limited is determinwed in response to the value of the derivative of the mathematical polynomial function.

BRIEF DESCRIPTION OF THE DRAWING

Comprehension of the invention is facilitated by reading the following detailed description, in conjunction with the annexed drawing, in which

FIGS. 5A and 5B are graphical representations that illustrate the analyses conducted as described under Protocol 1 herein.

DETAILED DESCRIPTION

Figure 1:
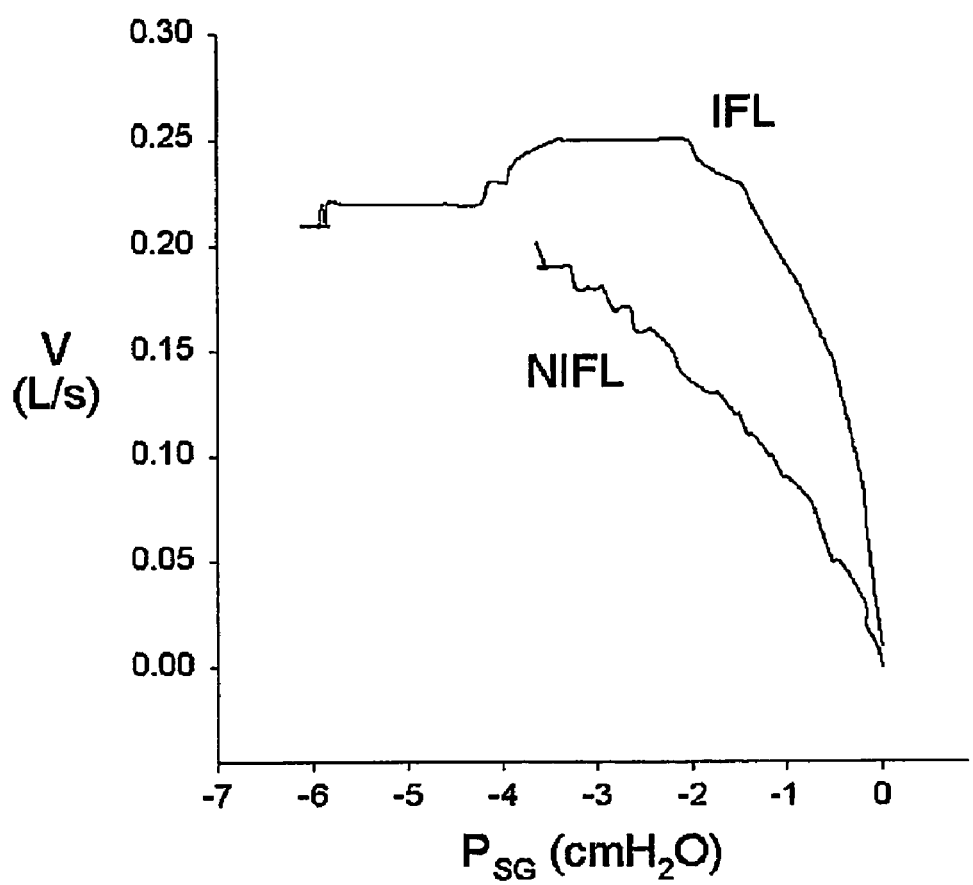
FIG. 1 is a graphical representation that shows pressure-flow loops illustrating NIFL and IFL breaths.

In developing the foundations of the present invention, the inventors herein consider a steady homogenous flow in a circular cylinder (the upper airway), with the assumption that the flow of air in the upper airway will expand without the loss or gain of heat. Consider a streamline of air, which connects two points $M_1$, the upstream pressure, which is atmospheric pressure in the present model, and $M_2$, the downstream pressure, which is equivalent to supraglottic pressure in the present model. For each point, there is a density ($\rho$), pressure (P), area (A), velocity (V) and flow (F) that characterize that point. In the modeling that follows, it should be noted that the goal is determination of the flow of the upper airway at the downstream pressure point, $M_2$. Flow, which is constant throughout the upper airway, is given by:

Total Energy=Kinetic Energy [T]+Potential Energy [E]+Internal Energy    (1)

Internal energy=0

Differentiate both sides of equation (1)

$$dK = dT + dE \quad (2)$$

$$T = \frac{1}{2}mV^2, E = pv \quad (3)$$

The gas unit mass (m) is defined according equation (4)

$$m = \rho v = 1, v = \frac{1}{\rho}, dv = d\left(\frac{1}{\rho}\right) \quad (4)$$

$$dK = VdV + Pdv \quad (5)$$

$$\frac{1}{2}V^2 + \int_{\rho_0}^{\rho_0{}^0} Pd\left(\frac{1}{\rho}\right) = const \quad (6)$$

Integrating by part the second term $$\frac{1}{2}V^2 + \frac{P}{\rho_0} - \frac{P}{\rho_0} - \int_{\rho_0}^{\rho} \frac{dP}{\rho} = const \quad (7)$$

Since the path is short then $\rho_2 \cong \rho_1 = \rho$    (8)

Rearrange and substitute $P = K\rho^\gamma (a), dP = K\gamma\rho^{\gamma-1}$    (8b)

Substitute (8b) in (7)

One obtains $$\frac{1}{2}V^2 + \frac{P}{\rho} - \frac{P}{\rho_0} - \left(\frac{1}{\gamma-1}\right)\left[\frac{K\rho_0^\gamma}{\rho_0} - \frac{K\rho^\gamma}{\rho}\right] = const \quad (9)$$

The terms in equation (9) can be reduced as $$\frac{P}{\rho_0} \cong \frac{P}{\rho} \text{ and, } \frac{K\rho_0^\gamma}{\rho_0} = const$$

Continuity equation $F = \rho_1 A_1 V_1 = \rho_2 A_2 V_2$    (10)

Solving for $V_1$:

$$V_1 = \frac{\rho_2 A_2}{\rho_1 A_1} V_2 = \Omega V_2 \quad (11)$$

Where, $$\Omega = \frac{\rho_2 A_2}{\rho_1 A_1} = \frac{A_2}{A_1} \quad (12)$$

The Bernoulli or energy equation for homogenous fluid such as air, on one streamline, through $M_1$, $M_2$ and neglecting the effect of gravity is:

$$\frac{P_1}{\rho_1} + \frac{1}{2}V_1^2 = \frac{P_2}{\rho_2} + \frac{1}{2}V_2^2 \quad (13)$$

Because air is a compressible, consideration needs to be given to the heat kinematics ratio $$\frac{\gamma}{\gamma-1}.$$

If the kinematics heat ratio is set as:

$$K = \frac{\gamma}{\gamma-1},$$

then equation (13) can be rewritten as derived by equation (9), as:

$$K\frac{P_1}{\rho_1} + \frac{1}{2}V_1^2 = K\frac{P_2}{\rho_2} + \frac{1}{2}V_2^2 \quad (14)$$

Because the path of the upper airway is short it may be assumed that $\rho_1 \cong \rho_2 = \rho$. Then equation 4 is rearranged as:

$$P_1 - P_2 = \frac{\rho}{2K}(V_2^2 - V_1^2) \qquad (15)$$

Substituting $V_1^2$ from equation 2:

$$P_1 - P_2 = \frac{\rho}{2K}(V_2^2 - \Omega^2 V_2^2) \qquad (16)$$

Solving for $V_2^2$:

$$V_2^2 = 2K\frac{(P_1 - P_2)}{\rho(1-\Omega^2)} \qquad (17)$$

Squaring both sides of equation 1, to obtain the flow squared at point $M_2$:

$$F^2 = \rho_2 A_2^2 V_2^2 \qquad (18)$$

Substituting for $V_2^2$ from equation 7:

$$F^2 = \frac{2\rho A_2^2 K}{(1-\Omega^2)}(P_1 - P_2) \qquad (19)$$

Rearranging:

$$F^2 = \frac{2\rho A_2^2 K}{(1-\Omega^2)} P_1 \left(1 - \frac{P_2}{P_1}\right) \qquad (20)$$

Taking the square root of both sides of equation 10, then one obtains $$F = \left(\frac{2\rho A_2^2 K P_1}{(1-\Omega^2)}\right)^{\frac{1}{2}} \left(1 - \frac{P_2}{P_1}\right)^{\frac{1}{2}} \qquad (21)$$

Let $$G = \left(\frac{2\rho A_2^2 K P_1}{(1-\Omega^2)}\right)^{\frac{1}{2}}$$

Therefore, flow through a streamline between two points, $M_1$ and $M_2$, is given by:

$$F = G\left(1 - \frac{P_2}{P_1}\right)^{\frac{1}{2}} \qquad (22)$$

Using Newton's expansion law:

$$(1+X)^N = 1 + NX + \frac{N(N-1)}{2!}X^2 + \frac{N(N-1)(N-2)}{3!}X^3 + \ldots$$

One obtains:

$$F = G + \frac{G}{2P_1}P_2 + \frac{G}{8P_1^2}P_2^2 + \frac{3G}{48P_1^3}P_2^3 + \ldots \qquad (23)$$

Letting, $$A = \frac{3G}{48P_1^3},$$

$$B = \frac{G}{8P_1^2},$$

$$C = \frac{G}{2P_1},$$

$$D = G$$

One then can substitute these coefficients into equation 23 to get a polynomial function that approximates flow (F) in terms of the supraglottic pressure. For this function, it is assumed that $P_1$ is atmospheric pressure, which is a constant, and $P_2=P$, which now is defined as the supraglottic pressure:

$$F = AP^3 + BP^2 + CP + D \qquad (24).$$

Per Newton's expansion law, the relationship between pressure and flow could also be predicted by a quadratic equation:

$$F = AP^2 + BP + C \qquad (25).$$

From the nature of a polynomial function the inventors predicted that a polynomial function would be expected to provide a better estimate of the pressure-flow relationship than can be achieved with the quadratic function for flow-limited breaths. This results from the fact that, for IFL breaths, the polynomial function is characterized by two deflections, as illustrated in FIG. 2. A two deflection relationship will more closely approximate the measured pressure-flow relationship of IFL breaths, which are characterized by a point of maximum flow, followed by a decrease and plateau in flow, as shown in FIG. 1.

FIG. 1 is a graphical representation that shows pressure-flow loops illustrating NIFL and IFL breaths. A breath was labeled IFL if there was a $\geq 1$ cmH$_2$O decrease in supraglottal pressure ($P_{SG}$) without any corresponding increase in flow (V) during inspiration.

Figure 2A:
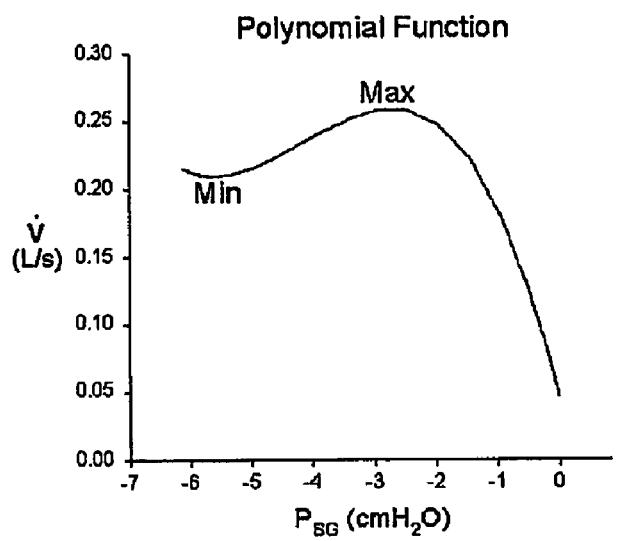
FIGS. 2A and 2B are graphical representations that illustrate the mathematical nature of a polynomial function (FIG. 2A) and a quadratic function (FIG. 2B).
Figure 2B:
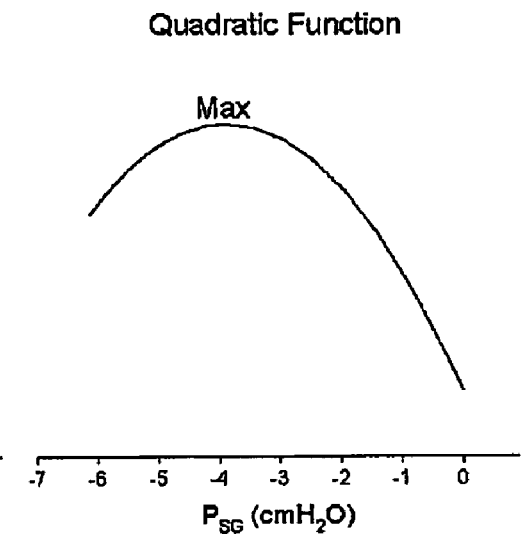

The quadratic function, on the other hand, is characterized by only one deflection, as shown in FIG. 2B. FIGS. 2A and 2B are graphical representations that illustrate the mathematical nature of a polynomial function (FIG. 2A) and a quadratic function (FIG. 2B). As shown, the polynomial function is characterized by two deflections, Min and Max, whereas the quadratic function is characterized by one deflection, Max.

While performing the initial curve-fitting analysis, as will be described in greater detail below, it is noted that the nature of the polynomial function, in contrast to the quadratic function, allows for the objective differentiation of IFL and NIFL breaths. In particular, it is noted that for the polynomial function, the maximal flow of the predicted relationship usually is located at the correspondingly same point as the measured maximal flow. In contrast, the predicted maximal flow for the quadratic function is at a more negative pressure. The inventors herein have hypothesized that a more objective result can be achieved by determining the presence of flow-limitation by examining derivative of the polynomial function. This would correspond to the slope of the pressure-flow relationship. The derivative of the polynomial function is:

$$\frac{dF}{dP} = 3AP^2 + 2BP + C \qquad (26)$$

Figure 3A:
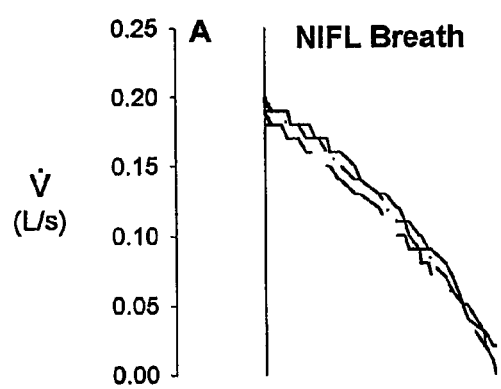
FIGS. 3A, 3B, 3C, and 3D are graphical representations that illustrate the hypothesized considerations regarding the ability of the polynomial and quadratic functions to distinguish between NIFL (FIGS. 3A and 3B) and IFL breaths (FIGS. 3C and 3D)
Figure 3C:
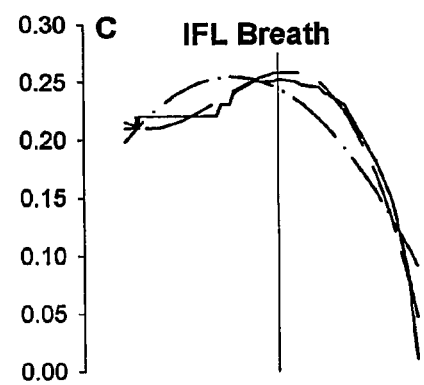
Figure 3B:
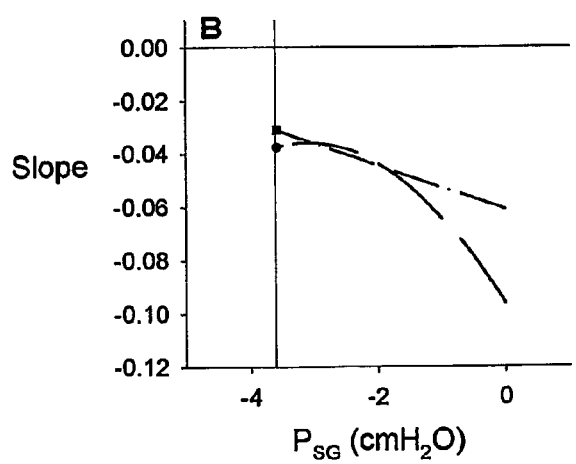
Figure 3D:
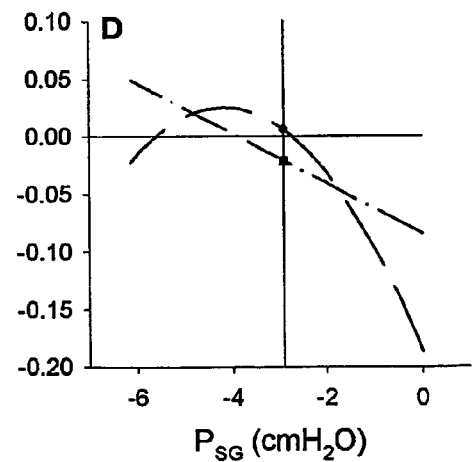

FIGS. 3A, 3B, 3C, and 3D are graphical representations that illustrate the hypothesized considerations regarding the ability of the polynomial and quadratic functions to distinguish between NIFL (FIGS. 3A and 3B) and IFL breaths (FIGS. 3C and 3D). The vertical straight line in all of these figures is located at the measured maximum flow (FIGS. 3A and 3C). There are shown in these figures the measured pressure-flow relationship (solid line) and the hypothesized polynomial (dashed line), and the quadratic (dash-dot line) relationships. In FIGS. 3B and 3D, there are shown the slopes of the predicted functions at increasing values of $P_{SG}$. The slope at the measured maximal flow for both, the polynomial and the quadratic function, remains negative for NIFL breaths (FIG. 3B). The slope of the polynomial function at the measured maximal flow becomes positive for IFL breaths, whereas the slope of the quadratic function remains negative (FIG. 3D).

Theoretically, for non-flow limited breaths, flow would continue to increase beyond the point of maximal flow if there were further decreases in supraglottic pressure. Therefore, the derivative of the polynomial function (or the slope of the pressure-flow curve) at the actual maximal flow is negative. This is illustrated in FIG. 3A which shows a NIFL breath and the theoretic relationship using the polynomial function. At the measured maximal flow, the slope of the theoretic pressure-flow relationship is negative, as illustrated in FIG. 3B. However, for breaths that demonstrate inspiratory flow limitation, there are no further increases in flow despite decreasing supraglottic pressure (FIG. 3C). Therefore, the slope or derivative of the polynomial function at the measured maximal flow is either zero or positive for flow-limited breaths (FIG. 3D). Therefore, at maximal flow, two cases can be determined from equation 26, as follows:

if $$1) \frac{dF}{dP} < 0,$$

the breath is non-flow-limited; and if $$2) \frac{dF}{dP} > 0 \text{ or } \frac{dF}{dP} = 0,$$

the breath is flow-limited.

By a similar analysis the inventors hypothesized that the derivative of the quadratic function cannot be used to determine if the pressure-flow relationship demonstrates flow limitation. The derivative of the quadratic function is given as:

$$\frac{dF}{dP} = 2AP + B \qquad (27)$$

However, if the quadratic function is used to characterize the pressure-flow relationship (FIGS. 3A and 3C), the derivative of the quadratic function cannot be used to distinguish between non-flow limited and flow-limited breaths. This is illustrated in FIGS. 3B and 3D, which shows that the derivative of the quadratic equation will be negative for both types of breaths. In other words, $$\frac{dF}{dP} < 0 \text{ for all breaths.}$$

In summary, theoretical considerations indicate that the relationship between flow and supraglottic pressure in the upper airway can be characterized by either a quadratic or polynomial function. However, based upon the theoretical considerations, the polynomial function was the better of the two functions to model the upper airway mathematically because it would provide the best fit compared to the actual pressure-flow relationship. Its derivative provides an objective and accurate methodology for the detection of inspiratory flow limitation.

In determining linear resistance, it is first understood that flow generally will proceed from an area of high pressure to an area of low-pressure, and that when the velocity of the air increases, the flow will change from laminar to turbulent. This is consistent with Bernoulli principle. In the laminar flow condition, the relation between pressure and flow is linear, and in the turbulent flow condition, the relationship is relatively non-linear. Therefore, in order to quantify the linear resistance, one needs to determine the flow in the laminar region, in accordance with the following principle for viscous flow:

$F \propto P^N$, where F is the flow, P is the pressure, and N is an exponent. If $N>1$, or $N<1$ then the flow is turbulent. If $N=1$ then the flow is laminar.

Referring once again to polynomial equation $F(P)=AP^3+BP^2+CP+D$, it can be seen that this equation has two phases of flow, i.e., laminar and turbulent. The equation is then recharacterized as follows:

$$F(P) = AP^3 + BP^2 + CP + D = F_1 + F_2$$

Where $F_1=AP^3+BP^2$ for turbulence flow, and $F_2=CP+D$ for laminar Flow. The reciprocal slope of the laminar flow is the first linear resistance:

$$R = \frac{1}{C} = \frac{\Delta P}{\Delta F}.$$

Thus, the polynomial coefficient C is used to determine the linear resistance.

Methodologies

The methodologies and corresponding data analyses in accordance with the present invention are organized into several major steps. The first step is the curve fitting. In order to determine the best function for effecting a correlation with measured results, actual data was curve fit by the inventors using five different mathematical functions. A selection then is made of the function that has the highest correlation $R^2$. In the second step, an error fit method is selected to achieve the least error fit. Finally, the analytical hypothesis is used to characterize the air flow. All these steps are performed on 50 breaths. At the final stage of the process, sensitivity analyses are performed to determine which function can best model the experimental data or pressure-flow loop.

Measurements and Manual Determination of Flow Limitation

For each breath, airflow (V) was measured by a pneumotachometer (Model 3700A, Hans Rudolph, Inc.) attached to a nasal mask. Supraglottic airway pressures were measured using a pressure-tipped catheter (Model TC-500XG, Millar Co.) threaded though the mask and positioned in the oropharynx just below the base of the tongue. Correct placement was verified by visually inspecting the catheter's position in the oropharynx.

Figure 4A:
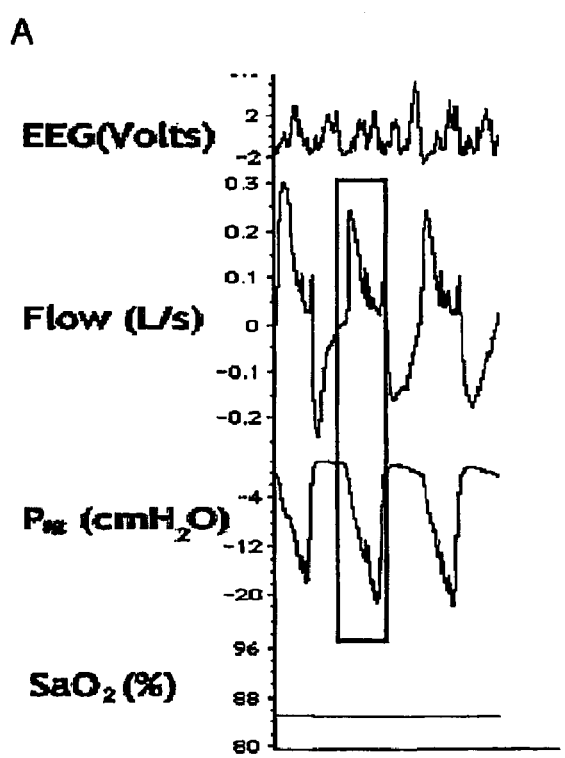
FIGS. 4A, 4B, 4C, and 4D are graphical representations that illustrate the sequences of the analyses.
Figure 4B:
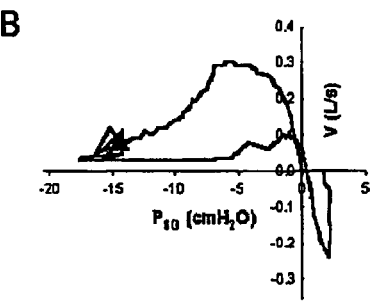
Figure 4C:
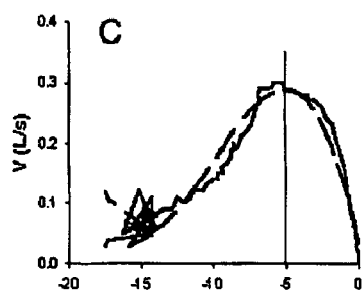
Figure 4D:
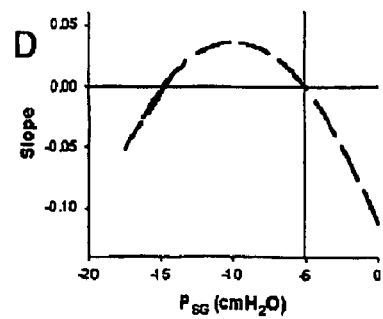

FIGS. 4A, 4B, 4C, and 4D are graphical representations that illustrate the sequences of the analyses. As shown in FIG. 4A, three breaths are represented from the raw tracing of a polygraph (not shown). The analysis herein was performed on the middle (boxed) breath. FIG. 4B shows the pressure loop of the indicated breath. The selected breath indicates flow limitation because there is no increase in flow despite a >1 cmH$_2$O increase in P$_{SG}$. FIG. 4C illustrates the curve fitting analysis, showing only the ascending limb of the inspiratory portion of the pressure-flow loop (solid line). The equation for the fitted curve is:

$$F(P) = -0.0005P^3 - 0.0151P^2 - 0.0302P - 0.1137.$$

Because the slope of the polynomial function is 0.001 (i.e., >0) at measured maximal flow (vertical line), the breath is characterized as IFL by the model. The EEG is the electroencephalogram, and SaO$_2$ is the arterial oxygen saturation.

During the studies, airflow and supraglottic pressure were recorded simultaneously with Biobench data acquisition software (National Instruments, Austin, Tex.) on a separate computer (FIG. 4A). For each breath, the onset of inspiration was defined as the sampling point at which V$_1$=0. In response to the rare occurrence where there was a shift in baseline, the nadir flow was determined and the flow values shifted appropriately. Because the Miller catheter provides relative pressures, PSG was set to zero for the inspiration onset sampling point and the remaining values for the breath were calculated. A pressure flow loop was generated (FIG. 4B) and the loop was analyzed for the presence of inspiratory flow limitation (IFL)(FIG. 1). A breath was labeled to be IFL if there was a ≧1 cmH$_2$O or greater decrease in supraglottic pressure without any corresponding increase in flow during inspiration. If the flow-pressure relationship did not meet this criterion, the breath was labeled as non-flow limited (NIFL).

All analyzed breaths in the following protocols were obtained during Stage 2 NREM sleep. Breaths from wakefulness were not analyzed, as IFL is not observed during wakefulness. As slow wave and REM sleep are not typically observed in the heavily instrumented subjects, breaths during these stages of sleep were not available for analysis. In addition, only breaths free from artifact were included in the analysis. All breaths were obtained from healthy polysomnography. The demographics of the subjects were presented within each protocol. Non-complaining adults who had volunteered for research studies in the laboratory were used as subjects. All subjects were free of sleep-disordered breathing, as measured by apneas and hypopneas, on baseline.

The first inquiry is whether the polynomial function best predicts the relationship between pressure and flow in the upper airway.

Step 1; Curve Fitting—First, the inventors performed a curve fitting step to model the upper airway mathematically. Sigma Stat 2.0 software {(FIGS. 4C and 5A)} was used in the analysis, the point of which was to determine which of following five regression equations (Table 1) best estimated inspiratory flow (the dependent variable) as a function of supraglottic pressure (the independent variable). This process is similar to performing a linear regression, in which the predicted relationship can be given by the equation: F(P)=AP+B.

TABLE 1

FUNCTIONS USED FOR CURVE FITTING

| | |
|---|---|
| One-term hyperbolic | $F(P) = AP/(B + P)$ |
| Two-term hyperbolic | $F(P) = AP/(B + P) + CP/(D + P) + FP$ |
| Exponential | $F(P) = Ae^{-BP} + Ce^{-DP}$ |
| Quadratic | $F(P) = AP^2 + BP + C$ |
| Polynomial | $F(P) = AP^3 + BP^2 + CP + D$ |

F(P), flow as a function of pressure;
A, B, C, D, and F, coefficients
e, exponential mathematical constant (~2.78)

However, since the pressure-flow relationship is not linear, the inventors herein used five non-linear regression functions. The first two are derived from the theoretical considerations above: quadratic and polynomial. The third, a single-term hyperbolic, has previously been proposed as an accurate predictor of the pressure-flow relationship. In addition, the inventors herein analyzed two additional functions: double-term hyperbolic and exponential. Neither the pressure nor flow values were transformed prior to the curve fitting. This analysis was performed on 20 breaths, 10 NIFL, 10 IFL derived from 4 subjects (1 male, 3 females, mean age 22±3 yrs, mean BMI 23.0±3.0 kg/m$^2$). For each calculated function, the inventors herein determined the coefficient of determination ($R^2$), which indicates how much of the variability in one variable (flow) is explained by knowing the value of the other (supraglottic pressure)(12). The $R^2$ for IFL and NIFL breaths were compared between the five functions using one-way repeated measures analysis of variance (ANOVA), with breath number as the repeated measure and the function as the factor for comparison. If there was a significant difference between the groups, a Student-Newman-Keuls test was performed to detect between group differences with P<0.05 set as the level for a significant test. The same test was performed on the combined groups of breaths.

Step 2: ErrorFit: To determine the degree of approximation between the pressure-flow relationship derived from either the quadratic or polynomial function to the actual pressure-flow relationship, the inventors herein determined the error-fit for 50 breaths, 25 each NIFL and IFL derived from 8 subjects (5 males, 3 females, mean age 25±4 years, mean BMI 26.2±4.8 kg/m$^2$). Only the quadratic and polynomial functions were studied based upon the results of the curve fitting analysis. An illustration of the concept of error-fit is given in FIGS. 5A and 5B.

FIGS. 5A and 5B are graphical representations that illustrate the analyses conducted as described under Protocol 1 herein. FIG. 5A is an example of curve fitting that shows the actual data points (○) and the predicted pressure-flow relationships if the points are fitted to a quadratic function (solid line) or the two-term hyperbolic function (dashed line). FIG. 5B illustrates an example of error fit that shows the actual (solid line) and predicted (dashed line) pressure-flow relationships. The predicted relationship uses the quadratic function. The shaded area is the graphical representation of the mathematical formula for error fit.

As noted, FIG. 5B shows the actual pressure-flow relationship for an IFL breath (solid line) and the predicted pressure-flow relationship using either the quadratic function (dashed line). The gray-shaded areas show the difference between the two relationships. The smaller the gray-shaded area, the smaller the error-fit and the more closely the predicted relationship approximates the actual pressure-flow relationship. The error-fit is a mathematical representation of this gray-shaded area. Mathematically, error fit is defined as:

$$100\left(\sum_{i}^{k} 1 - (y_k - y_i)\right) \quad (18)$$

where $$\sum_{i}^{k}$$

is the summation of a series of points, $y_k$ represents the points in the original function and $y_i$ represents the points in the fitted function. Using this formula, as the predicted pressure-flow relationship more closely approximates the actual relationship, the error-fit or difference between the two relationships decreases. The error-fit for IFL and NIFL breaths were compared between the five functions using one-way repeated measures analysis of variance (ANOVA), with the breath number as the repeated measure and the function as the factor for comparison. If there was present a significant difference between the groups, a Student-Newman-Keuls test was performed to detect the differences between the groups with $P<0.05$ set as the level for a significant test. The same test was performed on the combined groups of breaths.

The next question to be considered is whether the polynomial function objectively detects flow limitation?

Using the same 50 breaths on which the inventors herein determined the error-fit, the inventors herein determined the slope at the measured maximal flow for the polynomial equation. Per the hypothesis, if the slope at the measured maximal flow was <0, the inventors herein labeled the breath NIFL; if the slope at the measured maximal flow was $\geq 0$, the inventors herein labeled the breath IFL. The inventors calculated the sensitivity, specificity, positive predictive value (PPV) and negative predictive value (NPV) for the detection of IFL breaths by the polynomial model compared to the standard method (described at the beginning of the Methods section) using standard formulas.

To confirm the hypothesis that the slope at the measured maximal flow for the quadratic equation would be negative for both IFL and NIFL breaths, the inventors herein determined the slope at the measured maximal flow for the same 50 breaths. The inventors herein report the proportion of NIFL and IFL breaths with a negative slope.

To validate the results, the inventors herein then determined the slope at the measured maximal flow using the polynomial equation for 544 randomly selected breaths from 16 subjects without sleep-disordered breathing as measured by apneas and hypopneas (10 males, 10 females, mean age 30±8 yrs, mean BMI 25.2±4.3 kg/m²). Applying the hypothesis, the inventors herein labeled each breath as NIFL or IFL. The sensitivity, specificity, positive predictive value (PPV) and negative predictive value for the detection of IFL breaths are calculated by the polynomial model compared to the standard method using standard formulas.

Results

Protocol 1

The results showed that the polynomial and quadratic functions had better fits to the data than the single- and double-term hyperbolic and exponential functions. However, when using a test that determines the degree of correlation between the actual and experimental relationships (error-fit), only the polynomial function accurately predicts the pressure-flow relationship.

Sensitivity and specificity analyses in the development stage were higher for polynomial function than quadratic function using the derivative of each function. Therefore the inventors determined that polynomial function should be used for final validation of the mathematical models.

Curve Fitting: The results of the curve fitting are presented in Table 2. There was a significant difference between the $R^2$ values when all the breaths are combined and for the NIFL and IFL breaths when analyzed separately ($P<0.001$ for all three comparisons).

TABLE 2

$R^2$ VALUES FOR THE VARIOUS FUNCTIONS

|  | Quadratic | Polynomial | Single-Hyperbolic | Double-Hyperbolic | Exponential |
| --- | --- | --- | --- | --- | --- |
| IFL Breaths | 0.85 ± 0.10 | 0.90 ± 0.060 | 0.61 ± 0.14 | 0.79 ± 0.13 | 0.55 ± 0.32 |
| NIFL Breaths | 0.89 ± 0.06 | 0.92 ± 0.04 | 0.54 ± 0.20 | 0.70 ± 0.24 | 0.79 ± 0.24 |
| All Breaths | 0.88 ± 0.08 | 0.91 ± 0.05 | 0.57 ± 0.17 | 0.78 ± 0.19 | 0.67 ± 0.30 |

Values are means ± SE;
IFL, inspiratory flow limited;
NIFL, non-inspiratory flow limited For NIFL breaths, post-hoc testing showed that $R^2$ was significantly larger for the polynomial function compared to all other functions and that the quadratic function had a larger mean $R^2$ compared to other three functions. For IFL breaths, there was no difference in the mean $R^2$ values between the quadratic, polynomial and double hyperbolic functions. All three functions had larger mean $R^2$ values compared to the single-hyperbolic and exponential functions. For all the breaths combined, the mean $R^2$ was highest for the polynomial function. In addition, the $R^2$ values were higher for the quadratic equation compared to the other three functions. In summary, the polynomial and quadratic functions had better fits to the data than the single- and double-term hyperbolic and exponential functions. Therefore, further analysis was performed only on the quadratic and polynomial functions.

Error-Fit: Representative graphs depicting the relationship between the actual pressure-flow curve and the curve as predicted by either the quadratic or polynomial equations for one IFL and one NIFL breath is illustrated in FIG. 3. As can be seen, there is more overlap (less error) between the actual and predicted curves for the polynomial function than for the quadratic function. For the total group of 50 breaths, the error fits for the polynomial function were smaller on average than the quadratic function for the IFL breaths (2.0±2.7% vs. 25.0±22.2%, P<0.001), NIFL breaths (4.0±7.7% vs. 16.0±14.0%, P=0.003) and for all breaths combined (3.3±0.06% vs. 21.1±19.0%, P<0.001).

In summary, the curve-fitting of the pressure-flow relationship in the upper airway will result in a tight fit (high $R^2$) of the data only for the quadratic and polynomial functions. However, when using a test that determines the degree of correlation between the actual and experimental relationships (error-fit), only the polynomial function accurately predicts the pressure-flow relationship.

Protocol 2

Step 1: The sensitivity, specificity, PPV and NPV for the detection of flow limitation in the initial 50 breaths using the polynomial function is summarized in Table 3.

TABLE 3

SENSITIVITY/SPECIFICITY ANALYSIS

|  | Development Breaths (n = 50) | Validation Breaths (n = 544) |
|---|---|---|
| Sensitivity | 100 | 99 |
| Specificity | 100 | 99 |
| PPV | 100 | 97 |
| NPV | 100 | 99 |

PPV, positive predictive value;
NPV, negative predictive value

As the table illustrates, the use of the slope at maximal flow of the polynomial equation results in both high sensitivity and specificity for the determination of IFL breaths. PPV and NPV were also high. For the quadratic function, the inventors herein have confirmed that the majority of breathes of both NIFL (24 of 25, 96%) and IFL (22 of 25, 88%) IFL breaths had a negative slope, indicating that the quadratic function would be unhelpful in detecting IFL breaths.

Step 2: In the larger group of breaths, sensitivity and specificity remained high (Table 3, right column), as did the PPV and NPV.

In summary, in Protocol #2, a sensitivity/specificity analysis of the use of polynomial function was performed to detect IFL breaths compared to the standard method using a pressure-flow loop. This analysis indicates that the polynomial function has an excellent ability to predict the presence of flow-limitation in the pressure-flow relationship. In contrast, the quadratic function cannot be used to distinguish between IFL and NIFL breaths.

Findings

There are three major findings of this analysis. First, a polynomial equation, $F(P)=AP^3+BP^2+CP+D$, provides an estimation of the upper airway pressure-flow relationship with relative precision compared to other mathematical equations. Second, the derivative of this equation can be used to objectively and precisely determine the presence of inspiratory flow limitation. The Coefficients A, B, C, and D are part of the polynomial function and serve to identify the mathematical relation ship between pressure and flow or between flow or time. The A and B coefficients serve to describe principally the breath in turbulence, and the coefficients C and D describe laminar flow at low velocity. The derivative of function serves to specify the type of breath, particularly as to whether or not it is flow limited. Third, the coefficient C is useful to determine the linear resistance. The main requirement for the accurate determination of IFL using the polynomial function is a continuous and simultaneous measurement of flow and supraglottic pressure.

The relationship between flow and pressure in the upper airway during wakefulness was first described by Rohrer using the equation: $P=K_1*V+K_2*V^2$, where *V is flow and $K_1$ and $K_2$ are constants. A hyperbolic function (see Table 1) was shown to characterize better the upper airway pressure-flow relationship during sleep, as indicated by a correlation coefficient of 0.89 compared to 0.55 for the Rohrer equation. The characterization was better because the hyperbolic equation approximated the pressure-flow relationship for both NIFL and IFL breaths. Similarly, others recently found that the hyperbolic equation better characterized by the pressure-flow relationship, as evidenced by larger Pearson's square correlations for all breaths analyzed as well as for the subset of IFL breaths. In contrast, the inventors herein have found that a 3-term polynomial function best characterized the pressure-flow relationship during sleep. In addition, a hyperbolic function provided a poor characterization of the pressure-flow relationship.

Figure 6A:
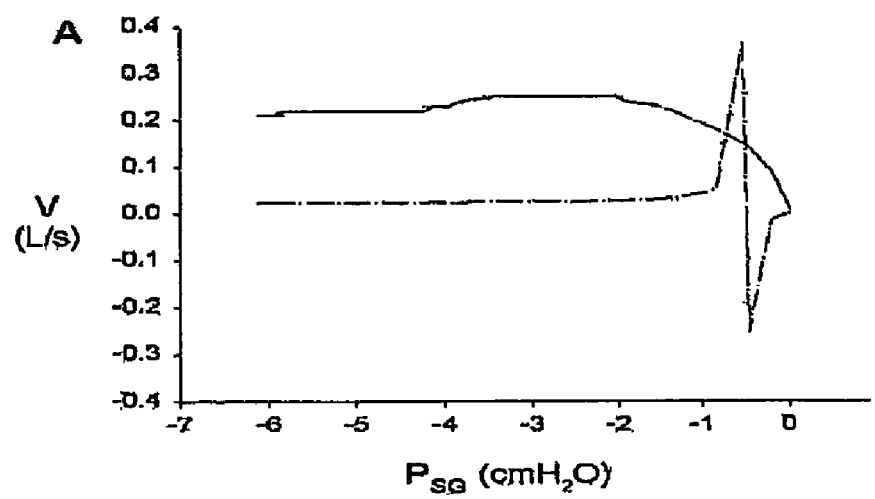
FIGS. 6A and 6B are graphical representations that show IFL breath and the fitted hyperbolic function when flow data is fitted to raw pressure data and when the data is fitted to pressure data that has been transformed to the absolute value.
Figure 6B:
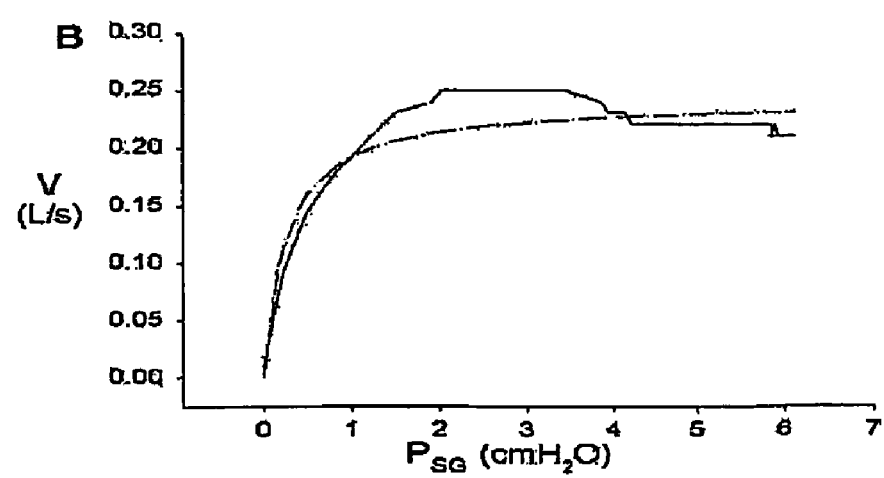

The importance of the use of the three term function is illustrated in FIGS. 6A and 6B. FIGS. 6A and 6B are graphical representations that show IFL breath and the fitted hyperbolic function when flow data is fitted to raw pressure data and when the data is fitted to pressure data that has been transformed to the absolute value. It is to be noted that in FIG. 6A, a hyperbolic curve provides a relatively poor representation for the actual flow relationship, whereas in FIG. 6B, the hyperbolic curve provides a reasonable representation of the pressure-flow relationship.

As can be seen from these figures, if positive values are used for pressure values, a hyperbolic curve closely approximates the actual pressure-flow relationship (FIG. 6A). The inventors nevertheless assert that the use of negative values for pressure is proper because the mathematical equations for curve fitting were derived to determine the relationship between the predicted and observed (actual), not transformed variables.

Limitation

The hypothesis hereinabove presented has a potential limitation, particularly in the application of Newton's expansion law. The inventors formulated a constant G that contains multiple parameters including density, area, atmospheric pressure, and kinematics heat ratio. Therefore, for G to be constant, these parameters must be assumed also to be constants during the flow between $M_1$ and $M_2$. The assumption that density and kinematic heat ratio are constants is based upon thermodynamic principles. It is believed that G is constant during any given breath, and the excellent agreement between the measured data, and polynomial function data supports the validity of this and other assumptions hereinabove set forth.

To ascertain the accuracy of mathematical detection of IFL, the inventors needed a "benchmark" for detection of flow limitation. An arbitrary degree of dissociation between pressure and flow for a 1 cm decrement in supraglottic pressure. However, the physiologic consequences of such mild degree of inspiratory flow limitation are not known. Conversely, mathematical methods and visual methods were remarkably reproducible indicating that this choice of parameter is valid for the recognition of the phenomenon. Accordingly, the present investigation provides an objective operational definition that can be used in future studies to ascertain physiologic relevance.

Inspiratory flow limitation in the present study was evaluated as a dichotomous variable. However, deviation from linearity between flow and pressure is a continuous variable. The present method detects flow limitation as defined by a plateau in flow only. Any other linear flow profile is classified as non-flow limitation. It can be argued that changes in the slope of the pressure-flow relationship indicate pharyngeal narrowing and turbulent flow. In fact, these were the breaths missed by the mathematical equation. However, it is doubtful that there is a physiologic significance of deviation from linearity without true flow limitation.

Finally, detection of inspiratory flow limitation in the present study required the use of supraglottic pressure measurement via a pharyngeal catheter and quantitative flow measurement using a sealed mask and a pneumotachometer. This combination is rather intrusive and may not be feasible for routine clinical use. As noted below, IFL can be detected from the flow versus time profile.

As noted, the percentage of breaths that are flow limited is related to BMI, upper airway resistance, and the presence of long-term facilitation. Therefore, a determination of the presence of flow-limitation is expected to provide an alternative metric to assess the relationship between SDB and daytime consequences such as excessive daytime sleepiness and cardiovascular morbidity, particularly in non-apneic forms of the syndrome.

Non-Invasive Approach

The inventors herein have established that there is a non-invasive aspect to the present invention. More specifically, the resistance in the Upper Airway is based on time flow. This is derived from the same hypothesis applied hereinabove in regard of the polynomial time flow function.

Since the flow is adiabatic, the first law of ideal gas at the site of supraglottic pressure (i.e., a mixed gas at constant temperature states) permits application of the thermodynamic Dalton model, as follows:

$$\frac{P_1}{P_2} = \frac{V_1}{V_2}; \quad (a)$$

pressure is proportional to volume, V is volume and Compressible Flow Polytrobic Cycle with constant specific heat or air:

$$PV^M = C \quad (b)$$

where $M = (\pm 1, \pm 1.3)$, for ideal gas $M = 1$, therefore $P = CV^{-1}$

-continued $$V = \int F dt = Ft © ) \text{ Volume} = \text{flow by time}$$

Given:

$$P = CV^{-1} \quad (1)$$

$$\text{Volume} = V = F \cdot t \quad (2)$$

Substitute in 1

$$P = C(F \cdot t)^{-1} \quad (3)$$

Divide (3) by F $$P/F = C/F^2 (l/t)$$

$$R = C/F^2 (l/t)$$

where t is the total time of inspiration/expiration.

Thus, in the laboratory environment flow pressure and time are measured as a routine medical assessment in order to determine flow limitation. Generally, one needs to look at both pressure and flow. Pressure is measured by the catheter and then it is compared to the criteria by visual inspection of a plateau of 1 cm of pressure and whether there is also present a decrease in flow.

However the inventors herein have found a polynomial function relationship between flow and time using derivatives. This relationship does not require that pressure be specifically measured, such as with a catheter, and therefore the novel method obviates the need for the invasive catheter. As described herein, this new method was validated by the inventors by comparing 440 breaths from multiple subjects to the results of the conventional method. The novel method produced results that were 98% correlated to the conventional method.

Software Implementation

The inventors herein have designed new codes that facilitate the rapid analysis of large quantities of data. Generally speaking, the code operates to form a moving average in different arrays and special curve fit of the function to the polynomial, and transfers data from MicroSoft Excel®. The algorithm performs calculations of derivatives and identifies the flow limitation by criteria. Unnecessary data is deleted. Moreover, the algorithm calculates the average of pressure flow from different breaths and draws all of them in stacked relation on one composite graph. Thus, there is formed a precise composite loop of several breaths added on top of each other.

An illustrative source code for a macro (Macro 1) is as follows:

```
Sub Group_Normalize_Chart( )
Cells.Select
ActiveWindow.Zoom = 75
Selection.NumberFormat = "0.00"
Range("A1:O25").Select
Selection.Cut Destination:=Range("P1:AD25")
Range("P1:AD25").Select
ActiveWindow.LargeScroll ToRight:=-1
Range("A1:O25").Select
Selection.Delete Shift:=xlUp
Dim BOTTOM As Long, COUNTER As Integer, X As Long, MVAL As Single
Dim STOPPER As Long
```

-continued

```
        BOTTOM = Cells(16384, 1).End(xlUp).Offset(-1, 0).Row
        COUNTER = 1
        Range("A3").Select
        X = 3
        Do Until Cells(X, 1).Row > BOTTOM
            Cells(X, 3).Value = Cells(X, 2).Value - MVAL
            Cells(X, 4).Value = Cells(X, 3).Value / Cells(X, 1).Value
            If Left(Cells(X - 1, 1).Value, 5) < > "Group" Then
                If Cells(X - 1, 1).Value < -0.0001 And Cells(X, 1).Value >= -0.0001 Then
                    Cells(X, 1).Select
                    Selection.EntireRow.Insert
                    BOTTOM = BOTTOM + 1
                    ActiveCell.Value = "Group " & COUNTER
                    If Abs(ActiveCell.Offset(-1, 0).Value) < Abs(ActiveCell.Offset(1,
                        0).Value) Then
                        MVAL = ActiveCell.Offset(-1, 1).Value
                    Else
                        MVAL = ActiveCell.Offset(1, 1).Value
                    End If
                    COUNTER = COUNTER + 1
                End If
            End If
            X = X + 1
        Loop
        InvertedPlot
        Find_Flex_Point
End Sub
Private Sub InvertedPlot( )
Dim TOP As Long, BOTTOM As Long, MYLOC As String
Dim MYTITLE As String, XPLOT As String, YPLOT As String
        CURRENT = ActiveSheet.Name
        Range("A1").Select
        Cells.Find(What:="Group 1", After:=ActiveCell, LookIn:=xlFormulas, LookAt_
            :=xlPart, SearchOrder:=xlByRows, SearchDirection:=xlNext, MatchCase:= _
            False).Activate
        Do Until IsEmpty(ActiveCell.Value) Or ActiveCell.Value = "END DATA"
            MYTITLE = ActiveCell.Value
            ActiveCell.Offset(1, 1).Select
            TOP = ActiveCell.Row
            BOTTOM = ActiveCell.End(xlDown).Row
            Range(Cells(TOP, 3).Address, Cells(BOTTOM, 3).End(xlDown).Address).Select
            MYLOC = Selection.Address
            Charts.Add
            ActiveChart.ChartType = xlXYScatterLines
            ActiveChart.SetSourceData Source:=Sheets(CURRENT).Range(MYLOC), _
                PlotBy:=xlColumns
            XPLOT = "=" & CURRENT & "'!R" & TOP & "C3:R" & BOTTOM & "C3"
            YPLOT = "=" & CURRENT & "'!R" & TOP & "C1:R" & BOTTOM & "C1"
            ActiveChart.SeriesCollection(1).XValues = XPLOT
            ActiveChart.SeriesCollection(1).Values = YPLOT
            ActiveChart.Location Where:=xlLocationAsNewSheet
            With ActiveChart
                .HasTitle = True
                .ChartTitle.Characters.Text = MYTITLE
                .Axes(xlCategory, xlPrimary).HasTitle = True
                .Axes(xlCategory, xlPrimary).AxisTitle.Characters.Text = "Pressure"
                .Axes(xlValue, xlPrimary).HasTitle = True
                .Axes(xlValue, xlPrimary).AxisTitle.Characters.Text = "Flow"
            End With
            Sheets(CURRENT).Activate
            Cells(BOTTOM + 1, 1).Select
        Loop
End Sub
Private Sub Find_Flex_Point( )
Dim X As Long, Y As Long, Z As Long, FIRST As Long, LAST As Long
    ' Find the top of the first group
    FIRST = Range("C3").End(xlDown).Offset(2, 0).Row
    ' Set the top of the table area
    Z = FIRST - 1
    Cells(Z, 7).Select
    ' Write table titles
    ActiveCell.Offset(0, -1).Value = "Group"
    ActiveCell.Value = "FLOW"
    ActiveCell.Offset(0, 1).Value = "Adj. Millar"
    ActiveCell.Offset(0, 2).Value = "Resistance"
    Z = Z + 1
    ' Loop through and find the flex point in each group
    Do Until IsEmpty(Cells(FIRST, 3).Value)
        ' find the bottom row of the current group
```

```
        LAST = Cells(FIRST, 3).End(xlDown).Row
        ' loop through the data to find the first value > 0.2.
        For X = FIRST To LAST
            If Cells(X, 1).Value >= 0.2 Then
                ' preserve the row number
                Y = X
                Exit For
            End If
            X = X + 1
        Next X
        ' determine if the prior value is closer than the current value
        If Abs(Cells(Y, 1).Value – 0.2) > Abs(Cells(Y – 1, 1).Value – 0.2) Then Y = Y – 1
        ' Calculate and write the desired value in column D
        ' Cells(Y, 4).Value = Cells(Y, 3).Value / Cells(Y, 1).Value
        ' Fill the table with the Group and values
        Cells(Z, 6).Value = Cells(FIRST – 1, 1).Value
        Cells(Z, 7).Value = Cells(Y, 1).Value
        Cells(Z, 8).Value = Cells(Y, 3).Value
        Cells(Z, 9).Value = Cells(Y, 4).Value
        ' Increment the counters to the proper location
        FIRST = LAST + 2
        Z = Z + 1
    Loop
    ActiveCell.End(xlDown).Offset(0, 2).Select
End Sub
```

This macro receives raw data corresponding, inter alia, to flow and time as the data is delivered to the polygraph (not shown). The data then is exported, in this specific illustrative embodiment of the invention, to a MicroSoft Excel® spread sheet (not shown). At this point, the macro is ready to do its action. The data in the spread sheet then is divided into breaths based on the fact that each breath would start with Flow=0 and that inspiration precedes expiration. Then, adjusted pressure would be added as a new column to make sure that the first coordinate of every breath would be (Pressure=0, Flow=0). This is normalizing the data, including time. Next, a fourth column is added as the resistance, where resistance=adjusted Pressure/Flow. Then, a table is created presenting the value of resistance at fixed flow (flow=0.20 L/s) for every breath. Finally, an X-Y graph is plotted for every breath where adjusted time in the x-axis and flow in the y-axis.

There is provided a second macro (Macro 2) that performs the same steps mention in the relation to Macro 1 up to calculating the adjusted pressure step. Then the adjusted time as x-axis and flow y-axis is considered. Next, a curve fitting of the inspiratory rising limb flow-time, a mathematical polynomial function $F(P)=At^3+Bt^2+Ct+D$. where A, B, C, and D are the coefficients (constants). The software will calculate the coefficients (A, B, C, D), and calculate the derivative of the mathematical model, which represents the slope. If the derivative at the maximum actual flow is zero or negative then the breath, as previously discussed, is inspiratory flow limited Although the invention has been described in terms of specific embodiments and applications, persons skilled in the art may, in light of this teaching, generate additional embodiments without exceeding the scope or departing from the spirit of the claimed invention. Accordingly, it is to be understood that the drawing and description in this disclosure are proffered to facilitate comprehension of the invention, and should not be construed to limit the scope thereof.

What is claimed is:

1. A method of measuring upper airway resistance of a human patient, the method comprising the steps of:

obtaining air pressure data from an air pressure data signal corresponding to a plurality of breathing cycles while the human patient is asleep;

obtaining air flow data from an air flow data signal corresponding to the plurality of breathing cycles while the human patient is asleep;

transferring the air pressure data and the air flow data to a processor;

storing the air pressure data and the air flow data in respective correlated storage regions of a matrix program system of the processor;

segregating the air pressure data and the air flow data in the matrix program of the processor into corresponding breathing cycles of the human patient;

computing normalized air pressure data to achieve a predetermined normalized air pressure value to correspond with a predetermined point for each breathing cycle of the human patient;

producing a correlation of the air flow data against normalized air pressure data;

curve-fitting onto the correlation of the air flow data against normalized air pressure data a curve corresponding to a predetermined multiple term mathematical function, the predetermined multiple term mathematical function is a three term polynomial function $F(P)=AP^3+BP^2+CP+D$, where A, B, and C are coefficients, and D is a constant;

computing the value of the coefficients of the predetermined multiple term mathematical function;

computing the derivative of the predetermined multiple term mathematical function; and computing a resistance corresponding to the reciprocal of coefficient C, whereby Resistance=1/C.

2. The method of claim 1, wherein said step of computing the derivative of the predetermined multiple term mathematical function corresponds to the relationship:

$$\frac{dF}{dP} = 3AP^2 + 2BP + C.$$

3. The method of claim 2, wherein there is provided the step of determining that a breath corresponds to snoring in response to the derivative of the three term polynomial function having a value of zero or positive, whereby $$\frac{dF}{dP} \geq 0 \rightarrow IFL.$$

4. The method of claim 2, wherein there is provided the step of determining that a breath does not correspond to snoring in response to the derivative or the three term polynomial function having a negative value, whereby $$\frac{dF}{dP} < 0 \rightarrow NIFL.$$

5. A method of determining a flow-limiting characteristic of the upper airway of a human patient, the method comprising the steps of:
obtaining air pressure data from an air pressure data signal corresponding to a plurality of breathing cycles while the human patient is asleep;
obtaining air flow data from an air flow data signal corresponding to the plurality of breathing cycles while the human patient is asleep;
transferring the air pressure data and the air flow data to a processor;
storing the air pressure data and the air flow data in respective correlated storage regions of a matrix program system of the processor;
segregating the air pressure data and the air flow data in the matrix program of the processor into corresponding breathing cycles of the human patient;
computing normalized air pressure data to achieve a predetermined normalized air pressure value to correspond with a predetermined point for each breathing cycle of the human patient; and
computing the flow-limiting characteristic of the upper airway of a human patient as a function of normalized air pressure data divided by corresponding air flow data;
wherein each breathing cycle of the human patient is determined in relation to the predetermined point thereof corresponding to the predetermined normalized air pressure value.

6. The method of claim 5, wherein the matrix program system is a spreadsheet program system, the air pressure data and the air flow data being arranged in respective spreadsheet columns correlated by rows.

7. The method of claim 6, wherein said step of computing normalized air pressure data comprises the further step of storing the normalized air pressure data in a respective spreadsheet column correlated by rows into corresponding breathing cycles of the human patient.

8. The method of claim 5, wherein there is further provided the step of computing the flow-limiting characteristic of the upper airway of a human patient for each of the plurality of breathing cycles.

9. The method of claim 5, wherein the predetermined normalized air pressure value corresponds to a zero value.

10. The method of claim 9, wherein each breathing cycle of the human patient is further determined in relation to the predetermined point thereof corresponding to the air flow data having a zero value.

11. The method of claim 5, wherein the air pressure data and the air flow data are sampled a plurality of times during each breathing cycle.

12. The method of claim 11, wherein said step of computing the flow-limiting characteristic of the upper airway of a human patient is performed a corresponding plurality of times during each breathing cycle.

13. The method of claim 12, wherein said step of computing the flow-limiting characteristic of the upper airway of a human patient is performed a corresponding plurality of times during each breathing cycle and during which the air flow data has a predetermined value.

14. The method of claim 13, wherein there is further provided the step of correlating the air flow data and the normalized pressure data to form a data correlation in a data correlation array, and the predetermined value of the air flow data is determined within a substantially linear portion of the data correlation.

15. The method of claim 14, wherein the predetermined value of the air flow data is approximately between 0.00 L/s and 0.22 L/s.

16. The method of claim 14, wherein the predetermined value of the air flow data is approximately 0.20 L/s.

17. The method of claim 14, wherein there is provided the further step of computing a slope of the correlated air flow data and normalized pressure data within the substantially linear portion of the data correlation.

18. The method of claim 13, wherein there is provided the further step of producing a data array corresponding to the flow-limiting characteristic wherein the normalized air pressure data corresponds to the x-axis and the air flow data corresponds to the y-axis.

19. A method of measuring upper airway resistance of a human patient, the method comprising the steps of:
obtaining air pressure data from an air pressure data signal corresponding to a plurality of breathing cycles while the human patient is asleep;
obtaining air flow data from an air flow data signal corresponding to the plurality of breathing cycles while the human patient is asleep;
transferring the air pressure data and the air flow data to a processor;
storing the air pressure data and the air flow data in respective correlated storage regions of a matrix program system of the processor;
segregating the air pressure data and the air flow data in the matrix program of the processor into corresponding breathing cycles of the human patient;
computing normalized air pressure data to achieve a predetermined normalized air pressure value to correspond with a predetermined point for each breathing cycle of the human patient;
producing a correlation of the air flow data against normalized air pressure data;
curve-fitting onto the correlation of the air flow data against normalized air pressure data a curve corresponding to a three term polynomial function $F(P)=AP^3+BP^2+CP+D$, where A, B, C, and D are coefficients; and
computing the value of the upper airway resistance of a human patient as an inverse function of coefficient C of the three term mathematical function, C, whereby Resistance=1/C.

20. The method of claim 19, wherein each breathing cycle is defined at an onset point where inspiratory flow is zero.

21. The method of claim 19, wherein each breathing cycle is defined at an onset point where supraglottic pressure has been normalized to zero.

22. The method of claim 19, wherein there as further provided the step of computing the derivative of the three term polynomial function in accordance with the relationship:

$$\frac{dF}{dP} = 3AP^2 + 2BP + C.$$

23. The method of claim 22, wherein there is further provided the step of determining the presence of inspiratory flow limitation in response to the derivative of the three term polynomial function.

24. The method of claim 19, wherein said step of obtaining air flow data from an air flow data signal comprises the further step of recording the air flow data signal on a polygraph.

25. The method of claim 24, wherein said step of storing the air pressure data and the air flow data in respective correlated storage regions of a matrix program system of the processor comprises the step of exporting the air pressure data and the air flow data to a first spreadsheet.

26. The method of claim 25, wherein there as further provided the step of plotting a graphical representation of adjusted time along the x-axis and flow along the y-axis.

27. The method of claim 26, wherein there is further provided the step of curve fitting an inspiratory rising limb flow-time curve to a mathematical polynomial function $F(P)=A t^3+B Ht^2+Ct+D$. where A, B, C, and D are coefficients.

28. The method of claim 27, wherein there is further provided the step of calculating a derivative of the mathematical polynomial function.

29. The method of claim 28, wherein there is further provided the step of exporting the value of the derivative of the mathematical polynomial function to a second spreadsheet.

30. The method of claim 29, wherein there is further provided the step of determining whether a breath is or is not flow limited, in response to the value of the derivative of the mathematical polynomial function.

* * * * *